United States Patent
Hirao et al.

(10) Patent No.: US 8,822,715 B2
(45) Date of Patent: Sep. 2, 2014

(54) METHOD FOR PRODUCING AROMATIC DIPHOSPHATES

(75) Inventors: Kiyoharu Hirao, Tokyo (JP); Katsuichi Ohtsuki, Osaka (JP); Hiroshi Tsuji, Osaka (JP); Hiroki Sato, Tokyo (JP)

(73) Assignee: Daihachi Chemical Industry Co., Ltd., Osaka (JP)

( * ) Notice: Subject to any disclaimer, the term of this patent is extended or adjusted under 35 U.S.C. 154(b) by 18 days.

(21) Appl. No.: 13/703,185

(22) PCT Filed: Jun. 21, 2011

(86) PCT No.: PCT/JP2011/064147
§ 371 (c)(1),
(2), (4) Date: Dec. 10, 2012

(87) PCT Pub. No.: WO2012/005109
PCT Pub. Date: Jan. 12, 2012

(65) Prior Publication Data
US 2013/0090490 A1    Apr. 11, 2013

(30) Foreign Application Priority Data
Jul. 6, 2010  (JP) .................................. 2010-153871

(51) Int. Cl.
| | |
|---|---|
| *C07F 9/12* | (2006.01) |
| *C09K 21/12* | (2006.01) |
| *B01J 27/138* | (2006.01) |
| *B01J 27/125* | (2006.01) |
| *B01J 27/16* | (2006.01) |

(52) U.S. Cl.
CPC ................. *C07F 9/12* (2013.01); *B01J 27/138* (2013.01); *B01J 27/125* (2013.01); *B01J 27/16* (2013.01); *C09K 21/12* (2013.01)
USPC ............................................................ 558/92

(58) Field of Classification Search
USPC ............................................................ 558/92
See application file for complete search history.

(56) References Cited

U.S. PATENT DOCUMENTS

| | | |
|---|---|---|
| 5,679,824 A | 10/1997 | Hirao et al. |
| 2004/0254390 A1 | 12/2004 | Tamura |

FOREIGN PATENT DOCUMENTS

| | | |
|---|---|---|
| EP | 0509506 | 10/1992 |
| JP | 05-001079 | 1/1993 |
| JP | 09-087290 | 3/1997 |
| JP | 2001-151787 | 6/2001 |
| JP | 2003-160712 | 6/2003 |
| WO | 02/100868 | 12/2002 |

OTHER PUBLICATIONS

Search report from International Application No. PCT/JP2011/064147, 2011.

*Primary Examiner* — Kristin Vajda
(74) *Attorney, Agent, or Firm* — Greenblum & Bernstein, P.L.C.

(57) ABSTRACT

A method for producing an aromatic diphosphate comprising: Step 1 which is a step where a specific aromatic monohydroxy compound having a steric hindrance group at ortho-positions is made to react with phosphorus oxyhalide in the presence of a Lewis acid catalyst and then the unreacted phosphorus oxyhalide is removed under a reduced pressure to give a specific; and Step 2 which is a step where the reaction product obtained in the above step is made to react with a specific aromatic dihydroxy compound in an amount of 0.5 mol to 1 mol of halogen contained in the reaction product in the presence of a Lewis acid catalyst to give a specific aromatic diphosphate.

11 Claims, No Drawings

METHOD FOR PRODUCING AROMATIC DIPHOSPHATES

TECHNICAL FIELD

The present invention relates to a method for producing an aromatic diphosphate useful as a phosphorus flame-retardant agent. More particularly, the present invention relates to a method for producing an aromatic diphosphate where production of by-products which deteriorate the physical properties of a phosphorus flame-retarding agent can be reduced without a purification treatment such as recrystallization using a solvent.

BACKGROUND ART

In order to impart flame retardancy to a thermoplastic or thermosetting resin, there has been adopted a method in which a flame-retardant agent is added in the process of molding the resin into an article. Examples of the flame-retardant agent include inorganic compounds, organophosphorus compounds, organohalogen compounds and halogen-containing organophosphorus compounds. Out of these compounds, organohalogen compounds and halogen-containing organophosphorus compounds exert an excellent flame-retardant effect. However, these halogen-containing compounds are pyrolyzed in the process of molding a resin to generate a hydrogen halide, which corrodes a metal mold, deteriorates the resin itself and causes coloration, degrading the working conditions. Another problem is that they generate a toxic gas such as a hydrogen halide, which is harmful to human bodies, when in a fire or incineration.

A halogen-free flame-retardant agent is therefore desired. Examples of such a flame-retardant agent include inorganic compounds such as magnesium hydroxide and aluminum hydroxide; and nitrogen compounds such as melamine cyanurate, melamine phosphate and melamine polyphosphate. However, the inorganic compounds and the nitrogen compounds have a significantly low flame-retardant effect and therefore need to be added in a large amount to obtain a sufficient effect, leading to degradation of physical properties intrinsic to the resin.

As a flame-retardant agent that is halogen-free and provides a relatively good flame-retardant effect, there may be mentioned organophosphorus compounds, among which organophosphates are generally used. As a representative organophosphate, triphenyl phosphate (TPP) is well known. However, TPP is less heat-resistant and more volatile.

While recently developed high-performance plastics such as engineering plastics and super engineering plastics require a temperature as high as approximately 300° C. for molding, TPP is thus not proof against such a high temperature.

For a flame-retardant agent having thermo stability and low volatility, therefore, studies have been made on flame-retardant agents in a powdered state that are high-purity, well-moldable, and advantageous in terms of handling, packaging and transportation, focusing on aromatic diphosphates represented by the general formula (I) of the present invention (see Japanese Unexamined Patent Publication No. HEI 5(1993)-1079 (Patent Document 1) and Japanese Unexamined Patent Publication No. HEI 9 (1997)-87290 (Patent Document 2)).

In the preparation method disclosed in Patent Document 1, a high-purity aromatic diphosphate is obtained by recrystallization or crystallization using a solvent in a purification step after a reaction. Such a method requires the steps of solid-liquid separation, drying and recycling of the solvent and has a low yield due to loss from dissolution to the solvent, and therefore is not necessarily advantageous in terms of preparation steps and costs, assuming in particular a large industrial scale.

Patent Document 2 therefore has proposed a method in which an aromatic diphosphate obtained is solidified and powdered without being subjected to a special purification process.

According to the method of Patent Document 2, however, a phosphorus compound having a hydroxyphenyl group represented by the general formula (II)

[Formula 1]

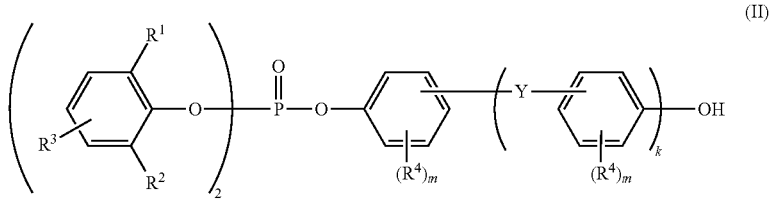

(II)

wherein $R^1$ and $R^2$ each independently is an alkyl group having 1 to 5 carbons; $R^3$ and $R^4$ each independently is a hydrogen atom or an alkyl group having 1 to 5 carbons; Y is a bonding arm or a —$CH_2$—, —$C(CH_3)_2$—, —S—, —$SO_2$—, —O—, —CO— or —N=N— group; k is 0 or 1; and m is an integer of 0 to 4, is present as a by-product in the aromatic diphosphate due to the absence of a special purification process.

When the aromatic diphosphate including the by-product is added as a flame-retardant agent to a thermoplastic resin such as polycarbonate, it undergoes a transesterification reaction during a molding process, it reacts with an end of a molecule of the resin pyrolyzed, or it gradually exerts an adverse effect as a molded article of the resin is used for a long term, to reduce the molecular weight of the resin, and as a result, the durability, physical properties, water resistance, hydrolysis resistance and heat resistance of the molded article of the resin will be reduced.

In addition, the by-product undergoes transesterification with the aromatic diphosphate being a main component under a high-temperature condition such as in the molding process to cause further increase of the by-product, reducing the purity of the main component.

Japanese Unexamined Patent Publication No. 2003-160712(Patent Document 3) discloses a flame-retardant composition based on a phosphorus compound having a hydroxyphenyl group represented by the general formula (II) of the present invention. Patent Document 3 considers application of the phosphorus compound as a reactive flame-retardant agent for an epoxy resin by using the functional group (hydroxyphenyl group) of the compound of the general formula (II).

However, in additive flame-retardant agents based on aromatic diphosphates represented by the general formula (I) of the present invention, compounds having a hydroxyphenyl group represented by the general formula (II) of the present invention are not preferable, because they cause the above-described problems.

RELATED ART DOCUMENTS

Patent Documents

Patent Document 1: Japanese Unexamined Patent Publication No. HEI 5 (1993)-1079
Patent Document 2: Japanese Unexamined Patent Publication No. HEI 9 (1997)-87290
Patent Document 3: Japanese Unexamined Patent Publication No. 2003-160712

SUMMARY OF THE INVENTION

Problems to be Solved by the Invention

It is an object of the present invention to provide a method for producing an aromatic diphosphate which is useful as phosphorus flame-retardant agent in high purity, in high yield and at low cost without subjecting to a purification treatment such as recrystallization using a solvent.

Thus, the problems of the present invention are to provide a method for producing an aromatic diphosphate of a general formula (I) where production of by-products deteriorating the physical properties of phosphorus flame-retardant agent can be reduced or, particularly, a phosphorus compound having a hydroxyphenyl group represented by the general formula (II) can be made 1% by area or less as determined by gel permeation chromatography (GPC).

Means for Solving the Problems

The present inventors have repeatedly conducted the studies for solving the above problems and, as a result, they have found that the above problems can be solved by the following method and, based on the above finding, they have accomplished the present invention.

Thus, in accordance with the present invention, there is provided a method for producing an aromatic diphosphate comprising:

Step 1 which is a step where an aromatic monohydroxy compound having a steric hindrance group (a group for giving steric hindrance) at ortho-positions represented by the following general formula (III)

[Formula 2]

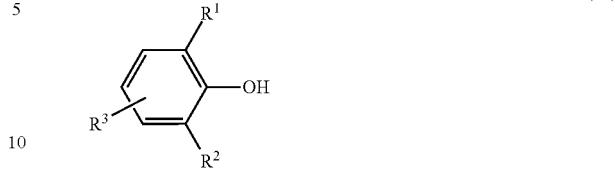

(III)

wherein $R^1$ and $R^2$ each independently is an alkyl group having 1 to 5 carbons; and $R^3$ is a hydrogen atom or an alkyl group having 1 to 5 carbons, is made to react with phosphorus oxyhalide in the presence of a Lewis acid catalyst and then the unreacted phosphorus oxyhalide is removed under a reduced pressure to give a diaryl phosphorohalidate represented by the following general formula (IV)

[Formula 3]

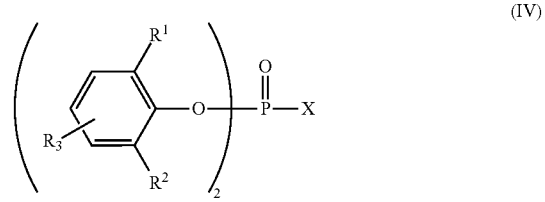

(IV)

wherein $R^1$, $R^2$ and $R^3$ are the same as those in the above general formula (III); and X is a halogen atom; and Step 2 which is a step where the reaction product obtained in the above step is made to react with an aromatic dihydroxy compound represented by the following general formula (V) in an amount of 0.5 mol to 1 mol of halogen contained in the reaction product

[Formula 4]

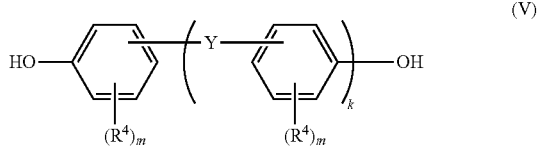

(V)

wherein $R^4$ is a hydrogen atom or an alkyl group having 1 to 5 carbons; Y is a bonding arm or a —$CH_2$—, —$C(CH_3)_2$—, —S—, —$SO_2$—, —O—, —CO— or —N=N— group; k is 0 or 1; and m is an integer of 0 to 4, in the presence of a Lewis acid catalyst to give an aromatic diphosphate represented by the following general formula (I)

[Formula 5]

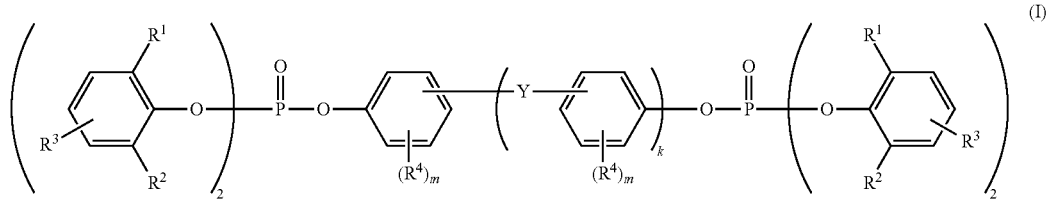

wherein $R^1$, $R^2$ and $R^3$ are the same as those in the above general formula (III); and $R^4$, Y, k and m are the same as those in the above general formula (V).

Effects of the Invention

The present invention can provide a method of producing an aromatic diphosphate which is useful as a phosphorus flame-retardant agent in high purity, in high yield and at low cost without subjecting to a purification treatment such as recrystallization using a solvent.

Thus, according to the present invention, the amount of the reaction material used in Step 2 in the production of an aromatic diphosphate of the general formula (I) in a two-step reaction is adjusted whereby production of by-products which deteriorate the physical properties of phosphorus flame-retardant agent can be reduced or, particularly, a phosphorus compound having a hydroxyphenyl group represented by the general formula (II) can be made 1% by area or less as determined by gel permeation chromatography (GPC).

Accordingly, an aromatic diphosphate obtained by the production method of the present invention is hardly deteriorated as a flame-retardant agent even by being exposed to high temperature upon molding of the thermoplastic resin or upon using the molded product for a long period of time, which can minimize deterioration of mechanical properties of the resin and which can impart excellent durability and flame retardancy to the resin.

The present invention can further provide a method for producing an aromatic diphosphate containing a phosphorus compound having a hydroxyphenyl group represented by the following general formula (II)

[Formula 6]

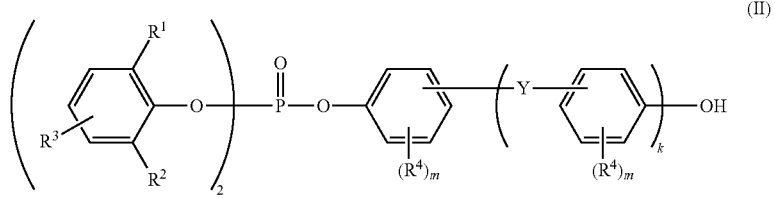

wherein $R^1$, $R^2$ and $R^3$ are the same as those in the general formula (III); and $R^4$, Y, k and m are the same as those in the general formula (V), as a by-product which is 1% by area or less as determined by gel permeation chromatography (GPC) and a method for producing an aromatic diphosphate which is 95% by area or more as determined by GPC.

Further, there is achieved more excellent above effect where an aromatic diphosphate of the general formula (I) and a phosphorus compound having a hydroxyphenyl group of the general formula (II) are a combination of tetrakis(2,6-dimethylphenyl)-m-phenylene bisphosphate with bis(2,6-dimethylphenyl)-3-hydroxyphenyl phosphate, tetrakis(2,6-dimethylphenyl)-p-phenylene bisphosphate with bis(2,6-dimethylphenyl)-4-hydroxyphenyl phosphate or tetrakis(2,6-dimethylphenyl)-4,4'-diphenylene bisphosphate with bis(2,6-dimethylphenyl)-4'-hydroxyphenyl-4-phenyl phosphate and, moreover, a combination of tetrakis(2,6-dimethylphenyl)-m-phenylene bisphosphate with bis(2,6-dimethylphenyl)-3-hydroxyphenyl phosphate or tetrakis(2,6-dimethylphenyl)-4,4'-diphenylene bisphosphate with bis(2,6-dimethylphenyl)-4'-hydroxyphenyl-4-phenyl phosphate.

Still further, more excellent above effect can be achieved when, in Step 1, the catalyst is 0.1 to 3.0% by weight of magnesium chloride to phosphorus oxyhalide; phosphorus oxyhalide is 0.5 mol to 1 mol of the aromatic monohydroxyl compound of the general formula (III); and the reaction is carried out under a reduced pressure at 50 to 250° C. and, furthermore when, in Step 2, the catalyst is 0.1 to 5.0% by weight of aluminum chloride to phosphorus oxyhalide used in Step 1 and the reaction is carried out under a reduced pressure at 50 to 250° C.

MODE FOR CARRYING OUT THE INVENTION

An aromatic diphosphate represented by the general formula (I) obtained by the production process according to the present invention (hereinafter, may be referred to as "aromatic diphosphate (I)") is characterized in that it contains, as a by-product, a phosphorus compound having a hydroxyphenyl group represented by the general formula (II) (hereinafter, may be referred to as "phosphorus compound (II) having a hydroxyphenyl group") in an amount of 1% by area or less as determined by GPC.

Regarding the content of the phosphorus compound (II) having a hydroxyphenyl group, "being 1% by area or less" as determined by GPC means that the content is "more than 0% by area and 1% by area or less". The lower limit of the content of the phosphorus compound (II) having a hydroxyphenyl group is preferably 0.01% by area, more preferably 0.001% by area and even more preferably 0.0001% by area. The upper limit thereof is preferably 0.9% by area, more preferably 0.8% by area and even more preferably 0.7% by area.

The content of the aromatic diphosphate (I) is preferably 95% by area or more as determined by GPC and, more preferably, 96% by area or more. Theoretically, although the upper limit of the content of the aromatic diphosphate (I) is 100%, it is preferably 99% by area, more preferably 99.5% by area and, still more preferably, 99.9% by area.

The reaction in the production process of the present invention is mainly in accordance with the reaction schemes as shown below.

1. Step 1

[Formulae 7]

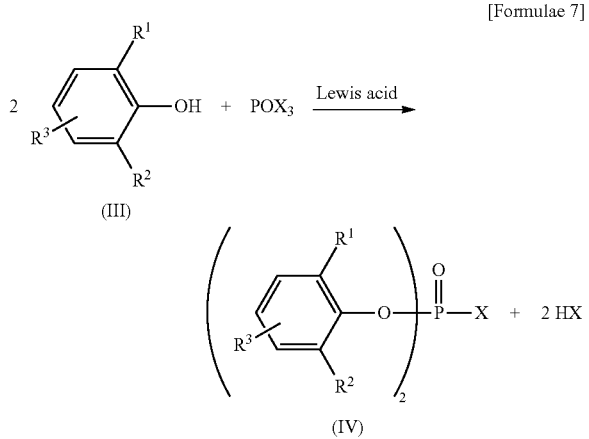

wherein $R^1$ and $R^2$ each independently is an alkyl group having 1 to 5 carbons; $R^3$ is a hydrogen atom or an alkyl group having 1 to 5 carbons; and X is a halogen atom.

The "alkyl group having 1 to 5 carbons" for $R^1$, $R^2$ and $R^3$ means a linear or branched alkyl group having 1 to 5 carbons such as, for example, methyl, ethyl, propyl, isopropyl, n-butyl, isobutyl, tert-butyl, n-pentyl, isopentyl and neo-pentyl, among which methyl group is particularly preferable due to the reason that the phosphorus content in the finally-produced aromatic diphosphate (I) becomes high.

Thus, specific examples of the aromatic monohydroxy compound (III) having a group for giving steric hindrance at the ortho position include 2,6-xylenol, 2,3,6-trimethylphenol and 2,4,6-trimethylphenol, of which 2,6-xylenol is particularly preferable due to the reason that the phosphorus content in the finally-produced aromatic diphosphate (I) becomes high.

Examples of the phosphorus oxyhalide include phosphorus oxychloride and phosphorus oxybromide, of which phosphorus oxychloride is particularly preferable in view of its cost and easy availability.

Examples of the Lewis acid catalyst used in the reaction in Step 1 include aluminum chloride, magnesium chloride, titanium tetrachloride, antimony pentachloride, zinc chloride and tin chloride, among which magnesium chloride is particularly preferable. These compounds may be used as a mixture of two or more kinds thereof.

The amount of the catalyst to use in Step 1 is preferably 0.1 to 3.0% by weight and, more preferably, in a range of 0.5 to 2.0% by weight with respect to the phosphorus oxyhalide.

Basically, the phosphorus oxyhalide is used usually at a proportion of 0.5 mole with respect to 1 mole of the aromatic monohydroxy compound (III). When the amount of the phosphorus oxyhalide is too large, the ratio of by-product arylphosphoro dihalidate will be higher, and a higher by-product condensate having three or more phosphorus atoms in a molecule will be produced between the arylphosphoro dihalidate and the aromatic dihydroxy compound (V) in Step 2. When the amount of the phosphorus oxyhalide is too small, the ratio of by-product triarylphosphate will be higher. In any case, the purity of the main component will be reduced.

However, the phosphorus oxyhalide and the aromatic monohydroxy compound (III) easily being evaporated together with a by-product hydrogen halide resulting from the reaction, and therefore the mole ratio between the compounds tends to alter, which is particularly significant in the case of an industrial scale. It is therefore preferable to appropriately adjust the mole ratio between the phosphorus oxyhalide and the aromatic monohydroxy compound (III) according to the production scale.

The reaction temperature is 50 to 250° C., preferably 100 to 200° C. The pressure in the reaction system may be reduced in order to remove the by-product hydrogen halide resulting from the reaction out of the reaction system and accelerate the reaction.

Though a reaction solvent is not necessarily needed in Step 1, it may optionally be used. Examples of the solvent include organic solvents such as xylene, toluene, chlorobenzene and dichlorobenzene.

When unreacted phosphorus oxyhalide remains, a higher by-product condensate having three or more phosphorus atoms in a molecule will be produced in Step 2 whereby purity of the main component lowers. Therefore, after completion of the reaction, phosphorus oxyhalide is removed under a reduced pressure of 30 kPa or less. When an organic solvent is used, it is removed at the same time upon reducing the pressure. Since the pressure reduction is to remove phosphorus oxyhalide, the pressure is preferably 20 kPa or less, and more preferably 10 kPa or less. An aromatic monohydroxy compound may also be removed at the same time.

2. Step 2

[Formulae 8]

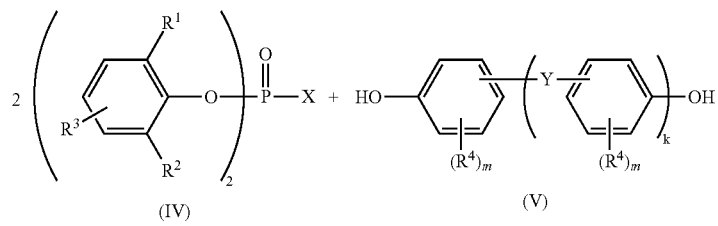

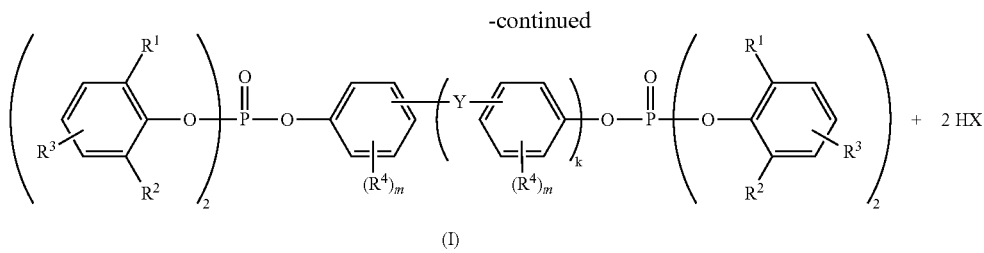

(I)

wherein $R^1$, $R^2$ and $R^3$ are the same as those in the general formula (III); $R^4$ is a hydrogen atom or an alkyl group having 1 to 5 carbons; Y is a bonding arm or a —$CH_2$—, —$C(CH_3)_2$—, —S—, —$SO_2$—, —O—, —CO— or —N=N— group; k is 0 or 1; and m is an integer of 0 to 4.

The "alkyl group having 1 to 5 carbons" represented by $R^4$ means a linear or branched alkyl group having 1 to 5 carbon atoms such as, for example, methyl, ethyl, propyl, isopropyl, n-butyl, isobutyl, tert-butyl, n-pentyl, isopentyl and neo-pentyl.

Thus, specific examples of the aromatic dihydroxy compound (V) include hydroquinone, resorcinol, pyrocatechol, 4,4'-biphenol, 2,2',6,6'-tetramethyl-4,4'-biphenol, bisphenol A, bisphenol S, bisphenol F, tetramethyl bisphenol A, tetramethyl bisphenol F, 4,4'-dihydroxydiphenyl ether and 4,4'-thiodiphenol, among which hydroquinone, resorcinol and 4,4'-biphenol are particularly preferable due to the reason that availability is easy and that the content of phosphorus in the finally-produced aromatic diphosphate (I) becomes high.

As the Lewis acid catalyst usable for the reaction in Step 2, the Lewis acid catalyst in Step 1 may be mentioned, and the Lewis acid catalyst used in Step 1 as is may be used for the reaction in Step 2 without being removed after the reaction in Step 1 or a further Lewis acid catalyst may be added. As the Lewis acid catalyst to add, aluminum chloride is particularly preferable. Alternatively, an amine such as, for example, triethylamine and tributylamine may be used instead of or in combination with the Lewis acid catalyst.

The amount of the catalyst to use in Step 2 is preferably 0.1 to 5.0% by weight to the phosphorus oxyhalide used in Step 1 and, more preferably, in a range of 0.5 to 5.0% by weight.

In order to obtain an aromatic diphosphate (I), it is necessary that an aromatic dihydroxy compound (V) in a theoretical amount for making all of diaryl phosphorohalidate (IV) into aromatic diphosphate (I) which is a phosphate of a condensate type or, in other words, an aromatic dihydroxy compound (V) in a stoichiometric amount to diaryl phosphorohalidate (IV) is made to react with diaryl phosphorohalidate (IV).

The expression reading "a theoretical amount (stoichiometric amount) for making all of diaryl phosphorohalidate (IV) into aromatic diphosphate (I)" means an amount which is necessary for substituting all halogen atoms contained in diaryl phosphorohalidate (IV) with aryl ester group and, to be more specific, it is 0.5 mole of aromatic dihydroxy compound (V) to 1 mole of diaryl phosphorohalidate (IV).

However, as mentioned above, it is not possible to prepare 100% of diaryl phosphorohalidate (IV) in Step 1 and "the reaction product obtained in Step 1" contains by-products such as aryl phosphorodihalidate in addition to diaryl phosphorohalidate (IV).

In view of the above, in order to obtain an aromatic diphosphate (I) of the present invention in which 95% by area or more, as determined by GPC, of aromatic diphosphate (I) is contained and the content of a phosphorus compound (II) having a hydroxyphenyl group as a by-product is 1% by area or less as determined by GPC, the amount of an aromatic dihydroxy compound (V) used in Step 2 is approximately determined as follows in the present invention.

Thus, calculation is conducted from the reaction products obtained in Step 1 or, in other words, from the total weight of diaryl phosphorohalidate (IV) and by-products such as aryl phosphorodihalidate as well as halogen concentrations contained therein. To be more specific, when the weight of reaction products after completing the Step 1 is A (grams) and the halogen concentration thereof is B (% by weight), the necessary molar numbers (M) of the aromatic dihydroxy compound (V) can be calculated from the following formula where C is atomic weight of halogen.

$$M = A \times (B/100)/C \times (1/2)$$

When the amount of the aromatic dihydroxy compound (V) used in Step 2 is adjusted as such, the aromatic diphosphate (I) of the present invention can be obtained.

The reaction temperature is 50 to 250° C., preferably 100 to 200° C. The pressure in the reaction system may be reduced in order to remove the by-product hydrogen halide resulting from the reaction out of the reaction system so as to accelerate the reaction.

After completion of the reaction, impurities such as the catalyst in the reactant are washed and removed as an after-treatment step by a commonly known method. For example, the reactant is brought into contact with an aqueous solution of an acid such as hydrochloric acid to extract the impurities into the aqueous solution.

On this occasion, an organic solvent may be added to prevent the aromatic diphosphate (I) from solidifying.

As the organic solvent, preferable is an organic solvent that allows more aromatic diphosphate (I) to dissolve therein at high temperature and less aromatic diphosphate (I) to dissolve therein at low temperature. Non-limiting examples of such an organic solvent include toluene, xylene, chlorobenzene, dichlorobenzene and a mixed solvent of two or more kinds thereof.

The temperature for the treatment is from room temperature to the boiling point of the aqueous solution. The amount of the organic solvent to use is not particularly limited as long as the aromatic diphosphate (I) is not precipitated at the temperature for the treatment, at least.

When the above-described production steps are carried out on an industrial scale, the phosphorus oxyhalide and the aromatic monohydroxy compound (III) are easily evaporated together with the by-product hydrogen halide produced in the preparation of the diaryl phosphorohalidate (IV) in Step 1, and therefore it is difficult to precisely generate 1 mole of the diaryl phosphorohalidate (IV) from 2 moles of the aromatic monohydroxy compound (III). That is, due to the evaporation of phosphorus oxyhalide and the aromatic monohydroxy compound (III), the number of moles of the diaryl phosphorohalidate (IV) generated falls below ½ molar equivalents of the number of moles of the aromatic monohydroxy compound (III) in Step 1. Besides, the larger the industrial scale is and the larger the amount of the by-product hydrogen halide produced per unit time in Step 1 is, the more significant such a phenomenon is.

Since Step 1 and Step 2 are usually carried out successively in the same reaction vessel on the industrial scale, Step 2 will be affected by the reaction in Step 1. That is, theoretically, the amount of the aromatic dihydroxy compound (V) in Step 2 should be ¼ molar equivalents of the amount of the aromatic monohydroxy compound (III), but actually falls below ¼ molar equivalents. In Step 2, therefore, the aromatic dihydroxy compound (III) is not completely consumed and remains unreacted, since ¼ molar equivalents of the amount of the aromatic monohydroxy compound (III) used in Step 1 is excess stoichiometrically. That is, some hydroxy groups of the aromatic dihydroxy compound (V) remain in the reaction.

As a result, the phosphorus compound (II) having a hydroxyphenyl group is contained in the aromatic diphosphate (I).

Here, the "industrial scale" referred to means that the total amount of starting materials including an organic solvent to be poured into a reaction vessel for subjecting the aromatic dihydroxy compound (V) and the diaryl phosphorohalidate (IV) to the reaction is on a scale of normal industrial production. On the scale, the specific total amount is preferably 5 liters or more, more preferably 30 liters or more, even more preferably 100 liters or more, and particularly preferably 300 liters or more.

In addition, the specific total amount of these materials is preferably 20000 liters or less, and more preferably 10000 liters or less considering constraint of the reactor.

The aromatic diphosphate (I) and the phosphorus compound (II) having a hydroxyphenyl group are preferably a combination of tetrakis(2,6-dimethylphenyl)-m-phenylene-bisphosphate with bis(2,6-dimethylphenyl)-3-hydroxyphenylphosphate, tetrakis(2,6-dimethylphenyl)-p-phenylene-bisphosphate with bis(2,6-dimethylphenyl)-4-hydroxyphenylphosphate or tetrakis(2,6-dimethylphenyl)-4,4'-diphenylenebisphosphate with bis(2,6-dimethylphenyl)-4'-hydroxyphenyl-4-phenylphosphate, among which the combinations of tetrakis(2,6-dimethylphenyl)-m-phenylene-bisphosphate with bis(2,6-dimethylphenyl)-3-hydroxyphenylphosphate and tetrakis(2,6-dimethylphenyl)-4,4'-diphenylene bisphosphate with bis(2,6-dimethylphenyl)-4'-hydroxyphenyl-4-phenylphosphate are particularly preferable.

Other than the phosphorus compound (II) having a hydroxyphenyl group as a by-product, the aromatic diphosphate (I) of the present invention generates an aromatic triphosphate represented by the general formula (VI):

[Formula 9]

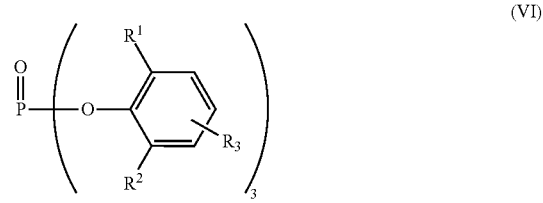

wherein $R^1$, $R^2$ and $R^3$ are the same as those in the general formula (III) (hereinafter, may be referred to as "aromatic monophosphate (VI)") and an aromatic triphosphate represented by the general formula (VII):

[Formula 10]

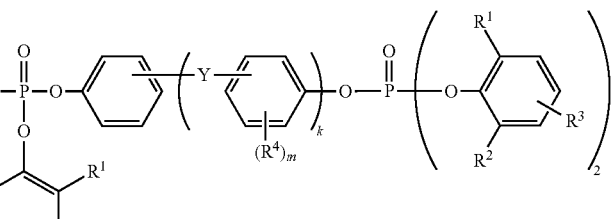

wherein $R^1$, $R^2$ and $R^3$ have the same meanings as for the general formula (III) and $R^4$, Y, k and m have the same meanings as for the general formula (V) (hereinafter, may be referred to as "aromatic triphosphate (VII)") at the same time.

However, the aromatic monophosphate (VI) and the aromatic triphosphate (VII) as such have no adverse effect on resin as having no hydroxyphenyl group.

3. Powdering Step

The oily matter obtained in Step 2 can be powdered by stressing the same with a kneader generally used for kneading plastic materials at a temperature 5 to 100° C. lower than the melting point of the aromatic diphosphate (I).

By "kneading" is meant, when a plastic material is mixed with several kinds of additives, dispersing the additives uniformly in the material by giving shear force to the material and the additives at the same time.

By "stressing" is meant the same as the "kneading" in that the temperatures of the materials fed to the kneader are equalized and, at the same time, shear force, that is, stress is given to the materials.

Generally, kneaders are categorized into batch kneaders such as mixing rolls, sigmate blade type kneaders and intensive mixers; and continuous kneaders such as high-speed twin-screw continuous mixers and extruder type kneaders. When these kneaders are used for solidification as in the present invention, the continuous kneaders are preferable as being capable of compressing a solidified product at the same time as the kneading. In terms of industrial use, in addition, the continuous kneaders are advantageous as having higher processing performance.

As a particularly suitable kneader, may be mentioned a ko-kneader type kneader, which is a kind of extruder type kneaders and has strong shear force, produces a great kneading effect and is capable of continuous solidification and powdering. However, the kneader is not particularly limited thereto as long as the kneader produces such effects.

In addition, the kneader includes a heating mechanism such as an electrical resistance band heater, a cast-in aluminum heater and a dielectric heating system, and a heating or cooling mechanism by distributing water or oil in a jacket provided to a cylinder or in a pipe provided to a screw, so that the temperature in the kneader can be controlled.

The inside of the kneader needs to be controlled to an appropriate temperature range. The most appropriate temperature range varies according to, in particular, viscosity, fluidity and frictional heat in the kneading as well as thermophysical properties of the oily matter to solidify, and properties of the apparatus to use. The temperature is generally 5 to 100° C. lower, preferably 10 to 70° C. lower, and more preferably 10 to 50° C. lower than the melting point of the aromatic diphosphate. When the temperature is in this range, an appropriate stress is applied to the compound in the kneader to achieve complete solidification and shortening of the solidification time. Using no solvent for the powdering, the method excludes the step of drying the powder and excludes need to consider purification and recycling of the solvent, being advantageous for industrial production.

Examples of the method for powdering the oily matter obtained in Step 2 further include purification processes such as a recrystallization method using an organic solvent and a fractionation distillation method.

Examples of the organic solvent to use in the recrystallization method include alcohols such as methanol, ethanol, n-propanol, isopropanol, n-butanol and isobutanol; ketones such as acetone, methyl ethyl ketone and methyl isobutyl ketone; aromatic hydrocarbons such as benzene, toluene, xylene and ethyl benzene; halogenated aromatic hydrocarbons such as chlorobenzene and dichlorobenzene; and organic compounds generally used as solvents.

In the production process of the present invention, the content of the phosphorus compound having a hydroxyphenyl group of the general formula (II) can be made 1% by area or less as determined by GPC and no purification treatment is necessary whereby the main object of the above recrystallization method is to pulverize an oily matter.

However, in the recrystallization method, the content of the phosphorus compound having a hydroxyphenyl group can be further reduced and, in addition, purification efficiency is higher than the pulverization using a kneader. Accordingly, the recrystallization method may be optionally adopted.

The aromatic diphosphate (I) obtained by the production process of the present invention is high-quality and usable as a flame-retardant agent for various thermoplastic resins and thermosetting resins.

Examples of the thermoplastic resins include polyethylene resins, chlorinated polyethylenes, polypropylene resins, polybutadiene resins, polystyrene resins, polyvinyl chloride resins, polyphenylene ether resins, polyphenylene sulfide resins, polycarbonate resins, ABS (acrylonitrile-butadiene-styrene) resins, high impact styrene resins, SAN (styrene-acrylonitrile) resins, ACS resins, polyamide resins, polyimide resins, polyester resins such a PET (polyethylene terephthalate) resin or PBT (polybutylene terephthalate) resin, polyacrylic resins, polymethacryl resins, polyetheretherketones, polyethersulfones, polysulfones, polyarylates, polyether ketones, polyether nitryls, polythioether sulfons, polybenzimidazoles, polycarbodiimides, liquid crystal polymers and composite plastics. They can be used independently or in combination of two or more kinds thereof.

Examples of the thermosetting resins include epoxy resins, polyurethane resins, polyimide resins, phenol resins, novolac resins, polyetherimide resins, melamine resins, urea resins, unsaturated polyesters and diallyl phthalate resins. They can be used independently or in combination of two or more kinds thereof.

Out of these resins, as a resin where functions of the aromatic diphosphate (I) obtained by the production process of the present invention can be fully achieved, examples thereof include engineering plastics and super engineering plastics, which are high-performance and have a high molding process temperature and heatproof temperature, such as polyphenylene ether resins, polyphenylene sulfide resins, polycarbonate resins, ABS (acrylonitrile-butadiene-styrene) resins, high impact styrene resins, SAN (styrene-acrylonitrile) resins, polyamide resins, polyimide resins, polyester resins, polyacrylic resins, polymethacryl resins, polyether ether ketone resins, polyether sulfone resins, polysulfone resins, polyarylate resins, polyether ketones, polyether nitrile resins, polythioether sulfon resins, polybenzimidazole resins, polycarbodiimide resins, liquid crystal polymers, composite plastics, epoxy resins, melamine resins and unsaturated polyester resins. In particular, polycarbonate resins, polyphenylene ether resins, ABS resins, rubber-modified styrene resins, polyester resins, polyamide resins and epoxy resins are preferable.

The aromatic diphosphate (I) obtained by the production process of the present invention is used at a proportion of usually 0.1 to 100 parts by weight, preferably 0.5 to 50 parts by weight, more preferably 1 to 40 parts by weight, and particularly preferably 3 to 30 parts by weight with respect to 100 parts by weight of the above-mentioned resin.

If necessary, the flame-retardant resin composition compounded with the aromatic diphosphate (I) prepared by the production process of the present invention may contain an additional component that is usually added to resins, to the extent that the effects of the original resin are not lessened. Examples of the additional component include other flame-retardant agents, anti-drip agents, antioxidizing agents, fillers, lubricants, modifying agents, odorants, antifungus agents, pigments, dyes, heat resisting agents, weather resisting agents, antistatic agents, ultraviolet absorbers, stabilizers, toughening agents, anti-blocking agents, wood flour and starches.

The method for adding the aromatic diphosphate (I) obtained by the production process of the present invention to the resin is not particularly limited, and examples thereof include a commonly known method in which the components are melted and kneaded with a general kneading apparatus such as a single-screw extruder, a twin-screw extruder, a Bumbury mixer, a kneader, a mixer and a roll.

The aromatic diphosphate (I) obtained by the production process of the present invention can be advantageously used for resins having a higher molding temperature, for example, a resin that is molded at 160° C. or higher in an embodiment, a resin that is molded at 180° C. or higher in a more preferable embodiment and a resin that is molded at 200° C. or higher in a particularly preferable embodiment.

When added to a resin as a flame-retardant agent and processed with a molding machine, the aromatic diphosphate (I) obtained by the production process of the present invention does not generate gas at its high processing temperature to provide a molded article of high quality having excellent heat resistance and coloration resistance.

The aromatic diphosphate (I) obtained by the production process of the present invention can provide a desired molded article when it is added to the resin followed by molding.

EXAMPLES

The present invention will be described in detail by way of examples and comparative examples below; however, the scope of the present invention is not limited to these examples.

In the following examples and comparative examples, the proportion of each component in the composition obtained is expressed in percentage of the area of the component (% by area) as determined by gel permeation chromatography (GPC). The apparatus and measurement conditions for the GPC are shown below.

Analyzer: product by Tosoh Corporation, model: HLC-8020

Column: product by Tosoh Corporation, model: TSKGEL G1000HXL (30 cm)×2

Column tank temperature: 40° C.

Solvent: tetrahydrofuran (for industrial use)

Solvent flow rate: 0.8 ml/minute

Detector: RI (built in the apparatus body, polarized refractive index detector)

Range: 16 samples

Amount of sample solution injected: 100 µl (looped tube)

Sample solution: solution obtained by dissolving approximately 0.05 g of sample in 10 ml of tetrahydrofuran

| Data processor: product by Tosoh Corporation, model: SC-8010 Data processing conditions: | |
|---|---|
| START TIME | 10.0 min |
| STOP TIME | 25.0 min |
| WIDTH | 10 |
| SENSITIVITY | 0.8 |
| DRIFT | 0.1 |
| MINIMUM AREA | 0.0 |
| MINIMUM HEIGHT | 0.0 |

Example 1

1. Step 1

To a one-liter four-necked flask equipped with a stirrer, a thermometer, a dropping device (funnel) and a hydrochloric acid collecting device (condenser connected with a water scrubber), 244 g of 2,6-xylenol as an aromatic monohydroxy compound (III), 20 g of xylene as a solvent and 1.5 g of magnesium chloride as a catalyst were put in. The resulting mixed solution was heated under stirring and, when the temperature of the mixed solution reached 120° C., 153 g of phosphorus oxychloride was added thereto dropwise over approximately 2 hours. After completion of the addition, the mixed solution was heated to gradually raise the temperature thereof up to 180° C. over 2 hours for reaction to collect 68 g of hydrogen chloride (hydrochloric acid gas) generated through the water scrubber. Thereafter, the pressure in the flask was gradually reduced to 20 kPa at the same temperature (180° C.), and unreacted phosphorus oxychloride and xylenol were removed over 1 hour to obtain 322 g of a reaction mixture including di-(2,6-xylyl)phosphoro chloridate as a diaryl phosphorohalidate (IV). In addition, the content percentage of chlorine in the reaction mixture was 10.7% by weight.

2. Step 2

Next, 53.5 g of resorcinol as an aromatic dihydroxy compound (V) (an amount stoichiometrically equivalent to that of the di-(2,6-xylyl)phosphoro chloridate) and 4.2 g of aluminum chloride as an additional catalyst were added to the reaction mixture obtained in Step 1. The resulting mixed solution was heated under stirring to gradually raise the temperature thereof up to 180° C. over 2 hours to cause a dehydrochlorination reaction. The reaction was continued at the same temperature (180° C.) for 2 hours, and the pressure in the flask was gradually reduced to 20 kPa, under which the reaction was further continued for 2 hours to obtain a crude product of an aromatic diphosphate (I).

3. After-treatment Step

The resulting crude product was heated to 85° C., and 90 g of xylene, 9 g of 35% aqueous hydrochloric acid and 140 g of water were added thereto, stirred at the same temperature (85° C.) for 1 hour and allowed to stand to separate an aqueous phase.

To the resulting mixture of the crude product and the solvent (xylene) (the concentration of the crude product was approximately 80% by weight), 5 g of 28% aqueous sodium hydroxide and 130 g of water were added. The resulting mixed solution was stirred at 85° C. for 1 hour and allowed to stand to separate an aqueous phase.

Subsequently an oil phase of the resulting mixed solution was washed with 130 g of water at a liquid temperature of 85° C. to obtain 430 g of the oil phase (the concentration of the aromatic diphosphate (I) was approximately 80% by weight). The xylene was removed from the resulting oil phase under a reduced pressure, and then steam distillation was performed at a temperature of 140° C. and a reduced pressure of 6 kPa to obtain 330 g of an oily matter including the aromatic diphosphate (I).

4. Powdering Step

To a 1-liter four-necked flask equipped with a thermometer and a stirrer having a rotation frequency display function (model: HEIDON TYPE 3000 H, product by Shinto Scientific Co., Ltd.), 320 g of the oily matter including the aromatic diphosphate (I) was put in, allowed to cool to a temperature of 60° C. under stirring at a low rotation frequency (approximately 100 rpm) and maintained at the same temperature (60° C.) with a hot water bath.

Subsequently, 0.1% by weight of the aromatic diphosphate (I) in a crystal state as a crystal nucleus was added to the object being solidified (oily matter), and the mixture was stirred at a rotation frequency of 200 rpm. As a result, the oily matter was completely solidified in 8 minutes.

The resulting solidified product weighing 320 g was white powder and had a melting point of 98 to 101° C.

In addition, the solidified product was measured for the composition by gel permeation chromatography (GPC) to show that an aromatic diphosphate (I) represented by Compound (1) accounted for 96.6% by area, a phosphorus compound (II) having a hydroxyphenyl group represented by Compound (2) accounted for 0.7% by area, an aromatic monophosphate (VI) represented by Compound (7) accounted for 2.1% by area and an aromatic triphosphate (VII) represented by Compound (8) accounted for 0.6% by area (see the structural formulae below).

Table 1 shows the result obtained together with the materials.

[Formulae 11]

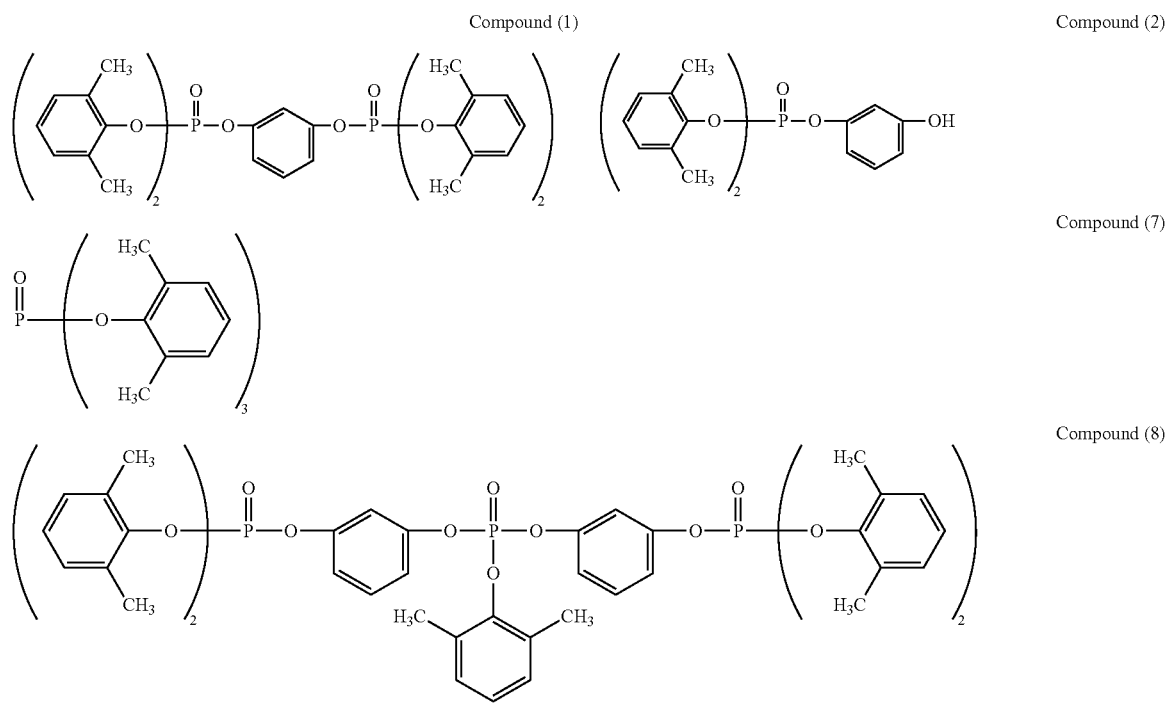

Example 2

A reaction mixture in an amount of 7741 g including di-(2,6-xylyl)phosphoro chloridate as the diaryl phosphorohalidate (IV) was obtained in the same manner as in Step 1 of Example 1 except that a 20-liter four-necked flask was used as a reaction vessel, and 5856 g of 2,6-xylenol as the aromatic monohydroxy compound (III), 480 g of xylene as the solvent, 36 g of magnesium chloride as the catalyst and 3672 g of phosphorus oxychloride were used. The content percentage of chlorine in the reaction mixture was 10.6% by weight.

Then, a crude product of the aromatic diphosphate (I) in an amount of 8200 g was obtained in the same manner as in Step 2 of Example 1 except that 1273 g of resorcinol as the aromatic dihydroxy compound (V) and 101 g of aluminum chloride as the additional catalyst were used.

Purification was performed in the same manner as in Example 1 except that 2160 g of xylene, 216 g of 35% aqueous hydrochloric acid, 3360 g of water, 120 g of 28% aqueous sodium hydroxide and 3120 g of water were added to the resulting crude product, and 3120 g of rinse water was used to obtain 7960 g of an oily matter including the aromatic diphosphate (I).

A powdering step was carried out in the same manner as in Example 1 except that a 20-liter four-necked flask was used, and 7920 g of the oily matter including the aromatic diphosphate (I) was used to obtain 7920 g of white powder.

The resulting white powder had a melting point of 98 to 101° C.

The resulting white powder was measured for the composition by GPC to show that the aromatic diphosphate (I) represented by Compound (1) accounted for 96.2% by area, the phosphorus compound (II) having a hydroxyphenyl group represented by Compound (2) accounted for 0.8% by area, the aromatic monophosphate (VI) represented by Compound (7) accounted for 2.3% by area and the aromatic triphosphate (VII) represented by Compound (8) accounted for 0.7% by area.

Table 1 shows the result obtained together with the materials.

Example 3

White powder in an amount of 320 g was obtained in the same manner as in Example 1 except that hydroquinone was used instead of resorcinol.

The resulting white powder had a melting point of 171 to 173° C.

The content percentage of chlorine in the reaction mixture in Step 1 was 10.6% by weight.

The resulting white powder was measured for the composition by GPC to show that an aromatic diphosphate (I) represented by Compound (3) accounted for 96.6% by area, a phosphorus compound (II) having a hydroxyphenyl group represented by Compound (4) accounted for 0.7% by area, the aromatic monophosphate (VI) represented by Compound (7) accounted for 2.1% by area and an aromatic triphosphate (VII) represented by Compound (9) accounted for 0.6% by area (see the structural formulae below).

Table 1 shows the result obtained together with the materials.

[Formulae 12]

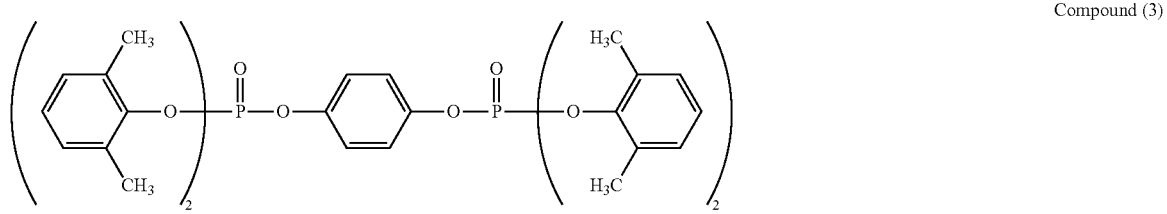

Compound (3)

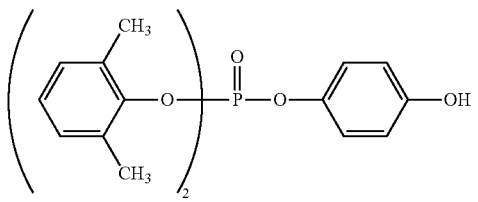

Compound (4)

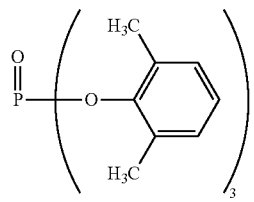

Compound (7)

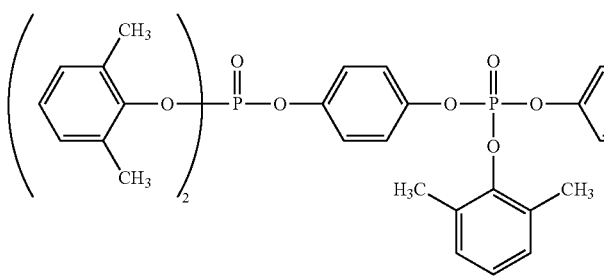

Compound (9)

Example 4

White powder in an amount of 7920 g was obtained in the same manner as in Example 2 except that hydroquinone was used instead of resorcinol.

The resulting white powder had a melting point of 171 to 173° C.

The content percentage of chlorine in the reaction mixture in Step 1 was 10.6% by weight.

The resulting white powder was measured for the composition by GPC to show that the aromatic diphosphate (I) represented by Compound (3) accounted for 96.4% by area, the phosphorus compound (II) having a hydroxyphenyl group represented by Compound (4) accounted for 0.7% by area, the aromatic monophosphate (VI) represented by Compound (7) accounted for 2.2% by area and the aromatic triphosphate (VII) represented by Compound (9) accounted for 0.7% by area.

Table 1 shows the result obtained together with the materials.

Example 5

White powder in an amount of 354 g was obtained in the same manner as in Example 1 except that 90 g of 4,4'-biphenol was used instead of resorcinol, and dichlorobenzene was used instead of xylene.

The resulting white powder had a melting point of 187 to 189° C.

The content percentage of chlorine in the reaction mixture in Step 1 was 10.4% by weight.

The resulting white powder was measured for the composition by GPC to show that an aromatic diphosphate (I) represented by Compound (5) accounted for 96.6% by area, a phosphorus compound (II) having a hydroxyphenyl group represented by Compound (6) accounted for 0.7% by area, the aromatic monophosphate (VI) represented by Compound (7) accounted for 2.1% by area and an aromatic triphosphate (VII) represented by Compound (10) accounted for 0.6% by area (see the structural formulae below).

Table 1 shows the result obtained together with the materials.

[Formulae 13]

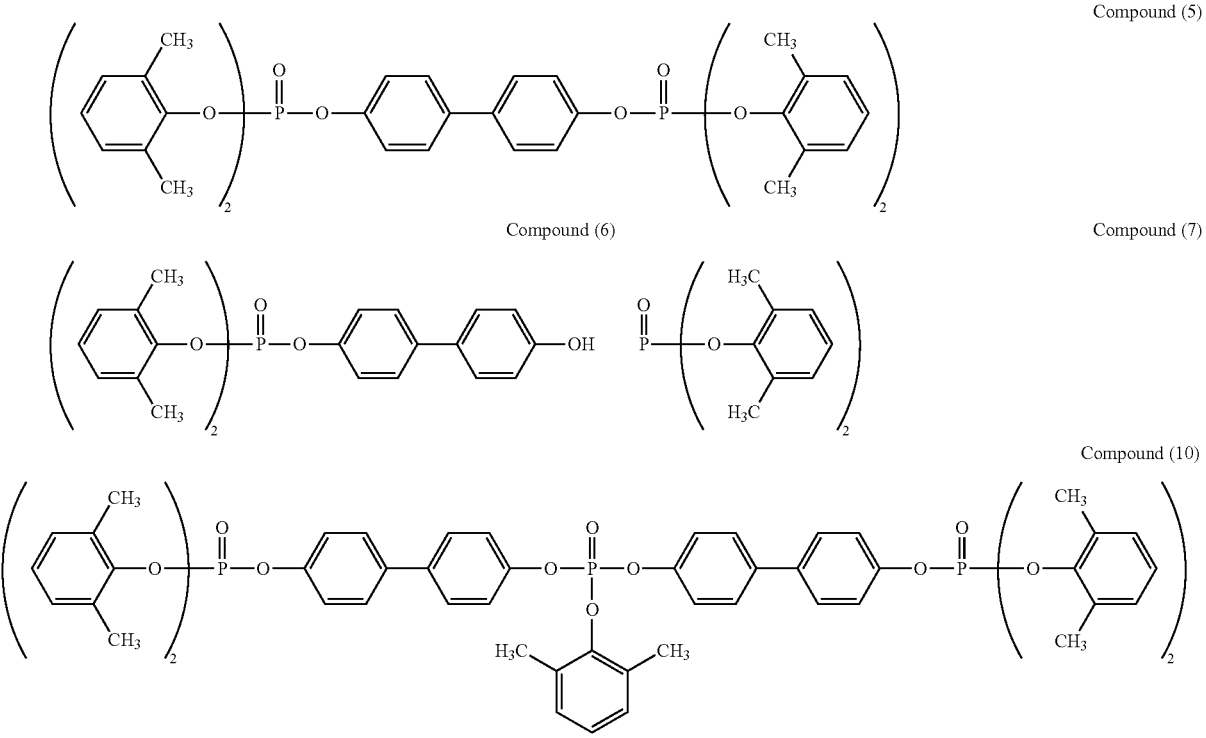

Example 6

White powder in an amount of 8800 g was obtained in the same manner as in Example 2 except that 2150 g of 4,4'-biphenol was used instead of resorcinol, and dichlorobenzene was used instead of xylene.

The resulting white powder had a melting point of 187 to 189° C.

The content percentage of chlorine in the reaction mixture in Step 1 was 10.4% by weight.

The resulting white powder was measured for the composition by GPC to show that the aromatic diphosphate (I) represented by Compound (5) accounted for 96.2% by area, the phosphorus compound (II) having a hydroxyphenyl group represented by Compound (6) accounted for 0.7% by area, the aromatic monophosphate (VI) represented by Compound (7) accounted for 2.4% by area and the aromatic triphosphate (VII) represented by Compound (10) accounted for 0.7% by area.

Table 1 shows the result obtained together with the materials.

Comparative Example 1

White powder in an amount of 322 g was obtained in the same manner as in Example 1 except that 55 g of resorcinol as the aromatic dihydroxy compound (V) (¼ molar equivalents with respect to the number of moles of 2,6-xylenol as the aromatic monohydroxy compound (III)) was used.

The resulting white powder had a melting point of 98 to 101° C.

The content percentage of chlorine in the reaction mixture in Step 1 was 10.7% by weight.

The resulting white powder was measured for the composition by GPC to show that the aromatic diphosphate (I) represented by Compound (1) accounted for 96.6% by area, the phosphorus compound (II) having a hydroxyphenyl group represented by Compound (2) accounted for 1.2% by area, the aromatic monophosphate (VI) represented by Compound (7) accounted for 1.8% by area and the aromatic triphosphate (VII) represented by Compound (8) accounted for 0.4% by area.

Table 1 shows the result obtained together with the materials.

Comparative Example 2

White powder in an amount of 8000 g was obtained in the same manner as in Example 2 except that 1320 g of resorcinol as the aromatic dihydroxy compound (V) (¼ molar equivalents with respect to the number of moles of 2,6-xylenol as the aromatic monohydroxy compound (III)) was used.

The resulting white powder had a melting point of 98 to 101° C.

The content percentage of chlorine in the reaction mixture in Step 1 was 10.6% by weight.

The resulting white powder was measured for the composition by GPC to show that the aromatic diphosphate (I) represented by Compound (1) accounted for 95.5% by area, the phosphorus compound (II) having a hydroxyphenyl group represented by Compound (2) accounted for 2.5% by area, the aromatic monophosphate (VI) represented by Compound (7) accounted for 2.0% by area and the aromatic triphosphate (VII) represented by Compound (8) accounted for 0.5% by area.

Table 1 shows the result obtained together with the materials.

Comparative Example 3

White powder in an amount of 322 g was obtained in the same manner as in Example 3 except that 55 g of hydroquinone as the aromatic dihydroxy compound (V) (¼ molar equivalents with respect to the number of moles of 2,6-xylenol as the aromatic monohydroxy compound (III)) was used.

The resulting white powder had a melting point of 171 to 173° C.

The content percentage of chlorine in the reaction mixture in Step 1 was 10.6% by weight.

The resulting white powder was measured for the composition by GPC to show that the aromatic diphosphate (I) represented by Compound (3) accounted for 96.3% by area, the phosphorus compound (II) having a hydroxyphenyl group represented by Compound (4) accounted for 1.5% by area, the aromatic monophosphate (VI) represented by Compound (7) accounted for 1.8% by area and the aromatic triphosphate (VII) represented by Compound (9) accounted for 0.4% by area.

Table 1 shows the result obtained together with the materials.

Comparative Example 4

White powder in an amount of 357 g was obtained in the same manner as in Example 5 except that 93 g of 4,4'-biphenol as the aromatic dihydroxy compound (V) (¼ molar equivalents with respect to the number of moles of 2,6-xylenol as the aromatic monohydroxy compound (III)) was used.

The resulting white powder had a melting point of 187 to 189° C.

The content percentage of chlorine in the reaction mixture in Step 1 was 10.4% by weight.

The resulting white powder was measured for the composition by GPC to show that the aromatic diphosphate (I) represented by Compound (5) accounted for 96.4% by area, the phosphorus compound (II) having a hydroxyphenyl group represented by Compound (6) accounted for 1.2% by area, the aromatic monophosphate (VI) represented by Compound (7) accounted for 2.0% by area and the aromatic triphosphate (VII) represented by Compound (10) accounted for 0.4% by area.

Table 1 shows the result obtained together with the materials.

TABLE 1

| | Aromatic monohydroxy compound (g) | Phosphorus oxyhalide (g) | Aromatic dihydroxy compound (g) | Composition (GPC % by area) | | | |
|---|---|---|---|---|---|---|---|
| | | | | Aromatic diphosphate | Phosphorus compound having hydroxyphenyl group | Aromatic monophosphate | Aromatic triphosphate |
| Example 1 | 2,6-xylenol 244 | Phosphorus oxychloride 153 | Resorcinol 53.5 | Compound (1) 96.6 | Compound (2) 0.7 | Compound (7) 2.1 | Compound (8) 0.6 |
| Example 2 | 2,6-xylenol 5856 | Phosphorus oxychloride 3672 | Resorcinol 1273 | Compound (1) 96.2 | Compound (2) 0.8 | Compound (7) 2.3 | Compound (8) 0.7 |
| Example 3 | 2,6-xylenol 244 | Phosphorus oxychloride 153 | Hydroquinone 53.5 | Compound (3) 96.6 | Compound (4) 0.7 | Compound (7) 2.1 | Compound (9) 0.6 |
| Example 4 | 2,6-xylenol 5856 | Phosphorus oxychloride 3672 | Hydroquinone 1273 | Compound (3) 96.4 | Compound (4) 0.7 | Compound (7) 2.2 | Compound (9) 0.7 |
| Example 5 | 2,6-xylenol 244 | Phosphorus oxychloride 153 | 4'4'-biphenol 90 | Compound (5) 96.6 | Compound (6) 0.7 | Compound (7) 2.1 | Compound (10) 0.6 |
| Example 6 | 2,6-xylenol 5856 | Phosphorus oxychloride 3672 | 4'4'-biphenol 2150 | Compound (5) 96.2 | Compound (6) 0.7 | Compound (7) 2.4 | Compound (10) 0.7 |
| Comparative Example 1 | 2,6-xylenol 244 | Phosphorus oxychloride 153 | Resorcinol 55 | Compound (1) 96.6 | Compound (2) 1.2 | Compound (7) 1.8 | Compound (8) 0.4 |
| Comparative Example 2 | 2,6-xylenol 5856 | Phosphorus oxychloride 3672 | Resorcinol 1320 | Compound (1) 95.0 | Compound (2) 2.5 | Compound (7) 2.0 | Compound (8) 0.5 |
| Comparative Example 3 | 2,6-xylenol 244 | Phosphorus oxychloride 153 | Hydroquinone 55 | Compound (3) 96.3 | Compound (4) 1.5 | Compound (7) 1.8 | Compound (9) 0.4 |
| Comparative Example 4 | 2,6-xylenol 244 | Phosphorus oxychloride 153 | 4'4'-biphenol 93 | Compound (5) 96.4 | Compound (6) 1.2 | Compound (7) 2.0 | Compound (10) 0.4 |

The results shown in Table 1 indicate that generation of the phosphorus compound (II) having a hydroxyphenyl group can be inhibited by using, in Step 2, the aromatic dihydroxy compound (V) in an theoretical amount needed for turning all the diaryl phosphorohalidate (IV) generated in Step 1 into a condensed phosphate that is, the aromatic diphosphate (I), in other words, in an amount stoichiometrically equivalent to the diaryl phosphorohalidate (IV).

It is also indicated that generation of the phosphorus compound (II) having a hydroxyphenyl group can be inhibited by adjusting the amount of the aromatic dihydroxy compound (V) to use in Step 2 even on an increased reaction scale (for example, comparison between Examples 1 and 2).

On the other hand, it is indicated that the amount of the phosphorus compound (II) having a hydroxyphenyl group tends to increase on an increased reaction scale when the amount of the aromatic dihydroxy compound (V) to use in Step 2 is not adjusted (for example, comparison between Comparative Examples 1 and 2).

Application examples of the aromatic diphosphate (I) obtained by the production process of the present invention are shown as hereunder in a form of Examples and Comparative Examples.

Examples 7 to 15

A modified PPE resin (product name: Noryl 731, manufactured by GE Plastics Japan Ltd.), a PC/ABS alloy resin (product name; NOVALLOY S-1500, manufactured by Daicel Polymer Ltd.) and an ABS resin (product name: CEVIAN V-500, manufactured by Daicel Polymer Ltd.) as resins, and a fluororesin (product name: Teflon, registered trademark, 6-J, manufactured by Du Pont-Mitsui Fluorochemicals Co., Ltd.) as an additive anti-drip agent were used.

Each formulation shown in Tables 2 to 4 was mixed with a mixer, and then passed through an extruder maintained at 250 to 300° C. to obtain compound pellets. The resulting pellets were put in an injection molding machine and molded at 250 to 300° C. to obtain a test piece.

The resulting test piece was measured for the flame retardancy, the Izod impact strength, the resin flowability (melt flow rate), the deflection temperature under load and the tensile strength in the manner described below.

In addition, as the durability test described below, the test piece treated with a thermohygrostat or a weather and light resistance testing machine was measured for the Izod impact strength and the melt flow rate.

Tables 2 to 4 show the results obtained together with the formulations of the resin compositions.
(1) Flame Retardancy (Vertical Flammability)
  Test method: according to UL-94 (average flame-out time of 5 samples)
  Test piece: 1.6 mm in thickness
  Evaluation: ranks V-0, V-1 and V-2 according to regulation
(2) Izod Impact Strength
  Test method: according to ASTM D-256
  Test piece: 3.2 mm in thickness
  Unit: J/m
(3) Melt Flow Rate (Resin Flowability)
  Test method: according to JIS K7210, operation A
  Temperature: 275° C. for modified PPE resin, 230° C. for PC/ABS alloy resin, 200° C. for ABS resin
  Load: 2.16 kg for modified PPE resin, 5 kg for PC/ABS alloy resin, 5 kg for ABS resin
  Unit: g/10 minutes When the molecular binding of the resin and the flame-retardant agent is broken by heat and load to reduce the molecular weight, the flowability of the resin composition increases. The flowability measured can therefore be a measure of the stability of the resin compositions.
(4) Deflection Temperature Under Load
  Test method: according to ASTM D-648
  Test piece: 6.4 mm in thickness
  Load: bending stress of 1.8 MPa
  Unit: ° C.
(5) Bending Strength
  Test method: according to ASTM D-790
  Test piece: 6.4 mm in thickness
  Unit: MPa The durability test was performed with the following testing machines.
(6) Thermohygrostat
  Testing machine: product by Tabai Espec Corp., product name: PLATINOUS RAINBOW PR-1G
  Testing tank temperature: 80° C.
  Testing tank humidity: 80% RH Test pieces treated for 6 hours and test pieces treated for 24 hours were measured for the Izod impact strength and melt flow rate, respectively. In Tables 2 to 4, the results are presented as 6HR-treatment w/ Rainbow and 24HR-treatment w/ Rainbow, each of which is a maintenance ratio (%) being a percentage of the initial value.
(7) Weather and Light Resistance Testing Machine
  Testing machine: product by Suga Test Instruments Co., Ltd., product name: Dewpanel Weather Meter DPWL-5
  Testing tank temperature: 60° C.
  Irradiation wavelength: 313 nm of peak wavelength (UV fluorescent lamp)
  Irradiation intensity: 2.0 mW/cm$^2$ Test pieces treated for 100 hours were measured for the Izod impact strength. In Tables 2 to 4, the results are presented as 100HR-treatment w/ Dewpanel, each of which is a maintenance ratio (%) being a percentage of the initial value.

Comparative Examples 5 to 13

The formulations shown in Tables 2 to 4 were used and test pieces were obtained in the same manner as in Examples 7 to 15 to be measured for the physical properties.

Tables 2 to 4 show the results obtained.

TABLE 2

| | m-PPE (parts by weight) | Flame retardant | Flame retardant (parts by weight) | Flame retardancy (UL-94) | Izod impact strength (J/m) | | | Melt Flow Rate (g/10 min) | | Deflection temp. under load (° C.) | Bending strength (Mpa) |
|---|---|---|---|---|---|---|---|---|---|---|---|
| | | | | | Initial | 6 HR-treatment w/ Rainbow | 100 HR-treatment w/ Dewpanel | Initial | 24 HR-treatment w/ Rainbow | | |
| Ex. 7 | 100 | Compound in Ex. 1 | 15 | V-0 | 100 | 71 Maintenance ratio 71% | 30 Maintenance ratio 30% | 11.3 | 14.1 Maintenance ratio 80% | 100 | 78 |
| Ex. 8 | 100 | Compound in Ex. 3 | 15 | V-0 | 102 | 75 Maintenance ratio 74% | 34 Maintenance ratio 33% | 11.8 | 14.6 Maintenance ratio 81% | 105 | 76 |
| Ex. 9 | 100 | Compound in Ex. 5 | 18 | V-0 | 105 | 77 Maintenance ratio 73% | 35 Maintenance ratio 33% | 12.1 | 14.6 Maintenance ratio 83% | 103 | 75 |

TABLE 2-continued

| | m-PPE (parts by weight) | Flame retardant | Flame retardant (parts by weight) | Flame retardancy (UL-94) | Izod impact strength (J/m) | | | Melt Flow Rate (g/10 min) | | Deflection temp. under load (° C.) | Bending strength (Mpa) |
|---|---|---|---|---|---|---|---|---|---|---|---|
| | | | | | Initial | 6 HR-treatment w/ Rainbow | 100 HR-treatment w/ Dewpanel | Initial | 24 HR-treatment w/ Rainbow | | |
| Com. Ex. 5 | 100 | Compound in Com. Ex. 1 | 15 | V-0 | 90 Initial strength 90% | 32 Maintenance ratio 36% | 23 Maintenance ratio 26% | 13.1 | 22 Maintenance ratio 60% | 102 | 77 |
| Com. Ex. 6 | 100 | Compound in Com. Ex. 3 | 15 | V-0 | 94 Initial strength 92% | 35 Maintenance ratio 37% | 24 Maintenance ratio 25% | 12.7 | 20.5 Maintenance ratio 62% | 104 | 77 |
| Com. Ex. 7 | 100 | Compound in Com. Ex. 4 | 18 | V-0 | 96 Initial strength 91% | 37 Maintenance ratio 39% | 27 Maintenance ratio 28% | 13.5 | 20.7 Maintenance ratio 65% | 102 | 75 |

TABLE 3

| | PC/ABS (parts by weight) | Flame retardant | Flame retardant (parts by weight) | Additive (parts by weight) | Flame retardancy (UL-94) | Izod impact strength (J/m) | | | Melt Flow Rate (g/10 min) | | Deflection temp. under load (° C.) | Bending strength (Mpa) |
|---|---|---|---|---|---|---|---|---|---|---|---|---|
| | | | | | | Initial | 6 HR-treatment w/ Rainbow | 100 HR-treatment w/ Dewpanel | Initial | 24 HR-treatment w/ Rainbow | | |
| Ex. 10 | 100 | Compound in Ex. 1 | 18 | 0.4 | V-0 | 551 | 342 Maintenance ratio 62% | 130 Maintenance ratio 23% | 16.3 | 20.7 Maintenance ratio 79% | 85 | 79 |
| Ex. 11 | 100 | Compound in Ex. 3 | 18 | 0.4 | V-0 | 540 | 351 Maintenance ratio 65% | 134 Maintenance ratio 25% | 16.6 | 20 Maintenance ratio 83% | 89 | 79 |
| Ex. 12 | 100 | Compound in Ex. 5 | 20 | 0.4 | V-0 | 545 | 376 Maintenance ratio 69% | 136 Maintenance ratio 25% | 16.5 | 19.4 Maintenance ratio 85% | 94 | 77 |
| Com. Ex. 8 | 100 | Compound in Com. Ex. 1 | 18 | 0.4 | V-0 | 471 Initial strength 85% | 138 Maintenance ratio 29% | 83 Maintenance ratio 18% | 17.8 | 32 Maintenance ratio 56% | 84 | 80 |
| Com. Ex. 9 | 100 | Compound in Com. Ex. 3 | 18 | 0.4 | V-0 | 475 Initial strength 88% | 152 Maintenance ratio 32% | 76 Maintenance ratio 16% | 17.9 | 30.5 Maintenance ratio 59% | 88 | 78 |
| Com. Ex. 10 | 100 | Compound in Com. Ex. 4 | 20 | 0.4 | V-0 | 469 Initial strength 86% | 188 Maintenance ratio 40% | 89 Maintenance ratio 19% | 17.8 | 27.3 Maintenance ratio 65% | 94 | 78 |

TABLE 4

| | ABS (parts by weight) | Flame retardant | Flame retardant (parts by weight) | Flame retardancy (UL-94) | Izod impact strength (J/m) | | | Melt Flow Rate (g/10 min) | | Deflection temp. under load (° C.) | Bending strength (Mpa) |
|---|---|---|---|---|---|---|---|---|---|---|---|
| | | | | | Initial | 6 HR-treatment w/ Rainbow | 100 HR-treatment w/ Dewpanel | Initial | 24 HR-treatment w/ Rainbow | | |
| Ex. 13 | 100 | Compound in Ex. 1 | 10 | V-2 | 166 | 108 Maintenance ratio 65% | 33 Maintenance ratio 20% | 5.2 | 6.5 Maintenance ratio 80% | 78 | 66 |
| Ex. 14 | 100 | Compound in Ex. 3 | 10 | V-2 | 170 | 120 Maintenance ratio 71% | 39 Maintenance ratio 23% | 5.3 | 6.2 Maintenance ratio 85% | 79 | 65 |

TABLE 4-continued

| | ABS (parts by weight) | Flame retardant | Flame retardant (parts by weight) | Flame retardancy (UL-94) | Izod impact strength (J/m) | | | Melt Flow Rate (g/10 min) | | Deflection temp. under load (° C.) | Bending strength (Mpa) |
| | | | | | Initial | 6 HR-treatment w/ Rainbow | 100 HR-treatment w/ Dewpanel | Initial | 24 HR-treatment w/ Rainbow | | |
|---|---|---|---|---|---|---|---|---|---|---|---|
| Ex. 15 | 100 | Compound in Ex. 5 | 12 | V-2 | 168 | 114 Maintenance ratio 68% | 42 Maintenance ratio 25% | 5.1 | 6.4 Maintenance ratio 80% | 82 | 67 |
| Com. Ex. 11 | 100 | Compound in Com. Ex. 1 | 10 | V-2 | 149 Initial strength 90% | 52 Maintenance ratio 35% | 22 Maintenance ratio 15% | 5.6 | 9.3 Maintenance ratio 60% | 77 | 67 |
| Com. Ex. 12 | 100 | Compound in Com. Ex. 3 | 10 | V-2 | 144 Initial strength 85% | 53 Maintenance ratio 37% | 18 Maintenance ratio 13% | 5.5 | 9.8 Maintenance ratio 56% | 80 | 69 |
| Com. Ex. 13 | 100 | Compound in Com. Ex. 4 | 12 | V-2 | 146 Initial strength 87% | 54 Maintenance ratio 37% | 22 Maintenance ratio 15% | 5.5 | 8.8 Maintenance ratio 63% | 83 | 69 |

The results shown in Tables 2 to 4 indicate that there is no big difference, a little difference if any, in the flame retardancy, the deflection temperature under load, the bending strength and the initial value of the melt flow rate between the molded articles of the flame-retardant resin compositions containing the aromatic diphosphate (I) of the present invention (Examples 7 to 15) and the molded articles of the flame-retardant resin compositions not containing the aromatic diphosphate (I) of the present invention (Comparative Examples 5 to 13). However, it is indicated that the former has larger initial values of the Izod impact strength.

Meanwhile, there is a very big and obvious difference in the Izod impact strength and the melt flow rate after the durability test between the former and the latter to indicate that the former is superior, prevented from losing the physical properties before the durability test.

That is, it is indicated that the molded articles of the flame-retardant resin compositions containing the aromatic diphosphate (I) of the present invention are superior in the Izod impact strength and the melt flow rate, in particular, superior in the durability against temperature and humidity.

The invention claimed is

1. A method for producing an aromatic diphosphate comprising:

Step 1 in which an aromatic monohydroxy compound having a steric hindrance group at ortho-positions represented by formula (III)

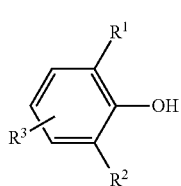
(III)

wherein $R^1$ and $R^2$ each independently is an alkyl group having 1 to 5 carbons; and $R^3$ is a hydrogen atom or an alkyl group having 1 to 5 carbons, is made to react with phosphorus oxyhalide in the presence of a Lewis acid catalyst and then the unreacted phosphorus oxyhalide is removed under a reduced pressure to give a diaryl phosphorohalidate represented by formula (IV)

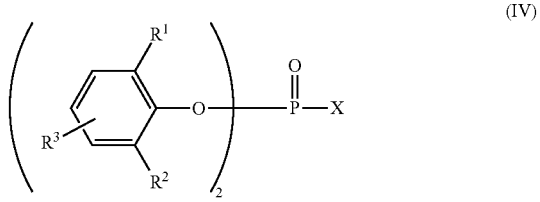
(IV)

wherein $R^1$, $R^2$ and $R^3$ are the same as those in formula (III); and X is a halogen atom; and Step 2 in which the reaction product obtained in Step 1 is made to react with an aromatic dihydroxy compound represented by formula (V) in an amount of 0.5 mol with respect to 1 mol of halogen contained in the reaction product

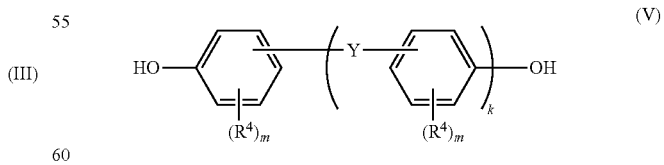
(V)

wherein $R^4$ is a hydrogen atom or an alkyl group having 1 to 5 carbons; Y is a bonding arm or a $-CH_2-$, $-C(CH_3)_2-$, $-S-$, $-SO_2-$, $-O-$, $-CO-$ or $-N=N-$ group; k is 0 or 1; and m is an integer of 0 to 4, in the presence of a Lewis acid catalyst to give an aromatic diphosphate represented by formula (I)

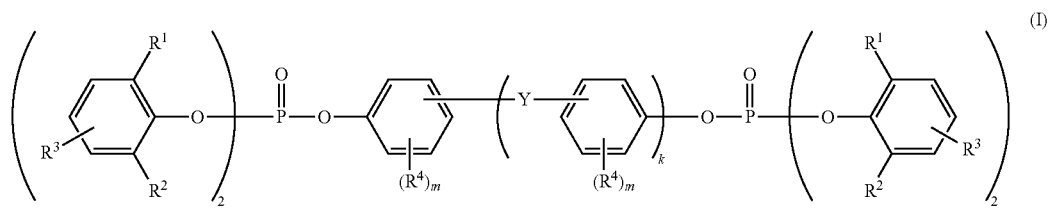

wherein R¹, R² and R³ are the same as those in formula (III); and R⁴, Y, k and m are the same as those in formula (V).

2. The method for producing the aromatic diphosphate of claim 1, wherein the aromatic diphosphate contains a phosphorus compound having a hydroxyphenyl group represented by formula (II)

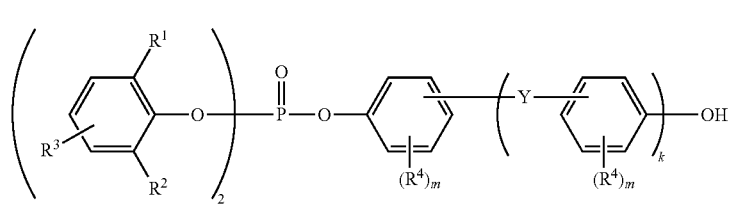

wherein R¹, R² and R³ are the same as those in formula (III); and R⁴, Y, k and m are the same as those in formula (V), as a by-product which is 1% by area or less as determined by gel permeation chromatography (GPC).

3. The method for producing the aromatic diphosphate of claim 1, wherein the content of the aromatic diphosphate is 95% by area or more as determined by GPC.

4. The method for producing the aromatic diphosphate of claim 2, wherein the phosphorus compound having a hydroxyphenyl group of formula (II) is a range of 0.01 to 0.9% by area.

5. The method for producing the aromatic diphosphate of claim 1, wherein the aromatic monohydroxy compound of formula (III) is 2,6-xylenol and the aromatic dihydroxy compound of formula (V) is hydroquinone, resorcinol or 4,4'-biphenol.

6. The method for producing the aromatic diphosphate of claim 2, wherein the aromatic diphosphate of formula (I) and the phosphorus compound having a hydroxyphenyl group of formula (II) is a combination of tetrakis(2,6-dimethylphenyl)-m-phenylene bisphosphate with bis(2,6-dimethylphenyl)-3-hydroxyphenyl phosphate, tetrakis(2,6-dimethylphenyl)-p-phenylene bisphosphate with bis(2,6-dimethylphenyl)-4-hydroxyphenyl phosphate or tetrakis(2,6-dimethylphenyl)-4,4'-diphenylene bisphosphate with bis(2,6-dimethylphenyl)-4'-hydroxyphenyl-4-phenyl phosphate.

7. The method for producing the aromatic diphosphate of claim 6, wherein the aromatic diphosphate of formula (I) and the phosphorus compound having a hydroxyphenyl group of formula (II) is a combination of tetrakis(2,6-dimethylphenyl)-m-phenylene bisphosphate with bis(2,6-dimethylphenyl)-3-hydroxyphenyl phosphate or tetrakis(2,6-dimethylphenyl)-4,4'-diphenylene bisphosphate with bis(2,6-dimethylphenyl)-4'-hydroxyphenyl-4-phenyl phosphate.

8. The method for producing the aromatic diphosphate of claim 1, wherein in Step 1, the catalyst is 0.1 to 3.0% by weight of magnesium chloride to phosphorus oxyhalide, the phosphorus oxyhalide is 0.5 mol to 1 mol of the aromatic monohydroxyl compound of formula (III), and the reaction is carried out under a reduced pressure at 50 to 250° C.

9. The method for producing the aromatic diphosphate of claim 1, wherein in Step 2, the catalyst is 0.1 to 5.0% by weight of aluminum chloride to phosphorus oxyhalide used in Step 1 and the reaction is carried out under a reduced pressure at 50 to 250° C.

10. The method for producing the aromatic diphosphate of claim 1, wherein includes an additional process to remove an unreacted phosphorus oxyhalide from the reaction product obtained in Step 1 under a reduced pressure of 30 kPa or less, before Step 2.

11. The method for producing the aromatic diphosphate of claim 1, wherein when the aromatic diphosphate of formula (I) obtained in Step 2 is an oily matter, includes an additional process to be powdered by stressing the oily matter at a temperature 5 to 100° C. lower than the melting point of the aromatic diphosphate.

* * * * *